United States Patent
Barrand

(10) Patent No.: US 9,642,732 B2
(45) Date of Patent: May 9, 2017

(54) ENDOVASCULAR GRAFT HAVING A CANNULATION POCKET

(71) Applicant: Cook Medical Technologies LLC, Bloomington, IN (US)

(72) Inventor: Zoe Barrand, Geenslopes (AU)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 14/887,960

(22) Filed: Oct. 20, 2015

(65) Prior Publication Data

US 2016/0038319 A1 Feb. 11, 2016

Related U.S. Application Data

(63) Continuation of application No. 14/323,556, filed on Jul. 3, 2014, now Pat. No. 9,168,123.

(30) Foreign Application Priority Data

Jul. 3, 2013 (AU) ................. 2013206712

(51) Int. Cl.
 *A61F 2/856* (2013.01)
 *A61F 2/954* (2013.01)
 (Continued)

(52) U.S. Cl.
 CPC ............... *A61F 2/954* (2013.01); *A61F 2/07* (2013.01); *A61F 2/856* (2013.01); *A61F 2/89* (2013.01);
 (Continued)

(58) Field of Classification Search
 CPC . A61F 2002/077; A61F 2/07; A61F 2002/072
 See application file for complete search history.

(56) References Cited

U.S. PATENT DOCUMENTS 6,129,756 A 10/2000 Kugler et al.
7,708,773 B2 5/2010 Pinchuk et al.
(Continued)

FOREIGN PATENT DOCUMENTS

EP 2491892 A1 8/2012
WO WO 2004/089249 A1 10/2004
(Continued)

OTHER PUBLICATIONS

Extended European Search Report for corresponding EP 142275118, dated Nov. 14, 2014, 8 pages.

*Primary Examiner* — Thomas J Sweet
*Assistant Examiner* — Wade P Shutte
(74) *Attorney, Agent, or Firm* — Brinks Gilson & Lione

(57) ABSTRACT

A stent graft for placement in a lumen of a patient is disclosed. The stent graft comprises: a main tubular body of a biocompatible graft material having a main lumen, the main tubular body having a proximal end and a distal end; a side arm extending from the main tubular body, the side arm having a side arm lumen, the side arm lumen being in fluid communication with the main lumen through a side arm opening in the main tubular body; and a cannulation pocket. The pocket comprises: an exit aperture positioned opposite the side arm opening; an entry aperture longitudinally spaced from the entry aperture in a direction toward the distal end of the main tubular body; and a wall, the wall laterally spaced from the main lumen so as to provide a guide surface for a cannula fed through the entry aperture.

20 Claims, 25 Drawing Sheets

(51) Int. Cl.
    *A61F 2/07*           (2013.01)
    *A61F 2/06*           (2013.01)
    *A61F 2/95*           (2013.01)
    *A61F 2/82*           (2013.01)
    *A61F 2/89*           (2013.01)

(52) U.S. Cl.
    CPC ... *A61F 2002/061* (2013.01); *A61F 2002/065* (2013.01); *A61F 2002/067* (2013.01); *A61F 2002/077* (2013.01); *A61F 2002/828* (2013.01); *A61F 2002/9511* (2013.01); *A61F 2230/0069* (2013.01)

(56) References Cited

U.S. PATENT DOCUMENTS

| | | |
|---|---|---|
| 2003/0181923 A1 | 9/2003 | Vardi |
| 2003/0233140 A1 | 12/2003 | Hartley et al. |
| 2004/0193254 A1 | 9/2004 | Greenberg et al. |
| 2005/0059923 A1 | 3/2005 | Gamboa |
| 2007/0250154 A1 | 10/2007 | Greenberg et al. |
| 2008/0228260 A1 | 9/2008 | Hannay |
| 2009/0043377 A1 | 2/2009 | Greenberg et al. |
| 2013/0046371 A1 | 2/2013 | Greenberg et al. |
| 2013/0211501 A1 | 8/2013 | Buckley et al. |

FOREIGN PATENT DOCUMENTS

| | | |
|---|---|---|
| WO | WO 2005/037141 A2 | 4/2005 |
| WO | WO 2007/022526 A1 | 2/2007 |

ENDOVASCULAR GRAFT HAVING A CANNULATION POCKET

RELATED APPLICATIONS

The application is a continuation of application Ser. No. 14/323,556, filed Jul. 3, 2014, which claims the benefit of priority to AU Patent Application No. 2013206712, filed Jul. 3, 2013, and entitled "Endovascular Graft Having A Cannulation Pocket," the entire contents of each of which are incorporated herein by reference.

BACKGROUND

1. Technical Field Text

This invention relates to medical devices and more particularly to devices which can be deployed by endovascular means into the vasculature of a patient.

2. Background

There exist endovascular stent grafts which can be deployed into the vasculature system so as to treat aortoiliac aneurysms. It is often necessary to produce stent grafts that have branches, the branches arranged to match anatomical branches in the vascular system.

Branched endovascular stent grafts for use in treating aortoiliac aneurysms require the insertion of a covered stent to bridge the gap between the endovascular graft and the internal iliac artery. A preferred method of introducing the covered stent is to insert the stent through the iliac/femoral artery on the contralateral side and guide the stent up and over to the ipsilateral side where it is deployed (the "up and over" approach). With some stent grafts, a fenestration or valve is provided in the wall of the stent graft to allow temporary access for a catheter to allow deployment of the covered stent through the iliac/femoral artery.

The above-described up and over access from the contralateral side is not ideal for all patients. Stent grafts having fenestrations or valves are difficult to design and manufacture for patients with short common iliacs because of the lack of room on the stent graft in the region of the common iliac. Furthermore, difficulties can arise in design of closing mechanisms for valved fenestrations.

It is an object of the present invention to provide an improved stent graft that ameliorates the aforementioned problem(s) or at least offers a useful choice Throughout this specification, when discussing the application of this invention to the aorta or other blood vessels, the term "distal" with respect to a prosthesis is intended to refer to a location that is, or a portion of the prosthesis that when implanted is, further downstream with respect to blood flow; the term "distally" means in the direction of blood flow or further downstream. The term "proximal" is intended to refer to a location that is, or a portion of the prosthesis that when implanted is, further upstream with respect to blood flow; the term "proximally" means in the direction opposite to the direction of blood flow or further upstream.

BRIEF SUMMARY

According to a first aspect of the invention, there is provided a stent graft for placement in a lumen of a patient, the stent graft comprising:
  a main tubular body of a biocompatible graft material having a main lumen, the main tubular body having a proximal end and a distal end;
  a side arm extending from the main tubular body, the side arm having a side arm lumen, the side arm lumen being in fluid communication with the main lumen through a side arm opening in the main tubular body; and
  a cannulation pocket, the pocket comprising:
    an exit aperture positioned opposite the side arm opening;
    an entry aperture longitudinally spaced from the entry aperture in a direction toward the distal end of the main tubular body; and
    a wall, the wall laterally spaced from the main lumen so as to provide a guide surface for a cannula fed through the entry aperture.

In one embodiment, the stent graft further comprises a distal sealing portion, the distal sealing portion sealable against the lumen of the patient.

In one embodiment, the distal sealing portion comprises a distal sealing stent, the distal sealing stent expandable to seal the distal sealing portion of the stent graft against the lumen of the patient.

In one embodiment, the side arm is angled with respect to the main tubular body such that the side arm lumen extends laterally and distally from the main lumen.

In one embodiment, the stent graft further comprises a central external zig-zag self-expanding stent which extends around both the main tubular body and a portion of the side arm, the central stent expandable so that the main lumen and the side arm lumen are each biased open allowing fluid to flow freely there-through.

In one embodiment, the stent graft further comprises a temporary diameter reduction constraint arrangement, the arrangement comprising:
  a release wire; and
  a plurality of loops of thread, each loop engaged with the release wire and engaged around a proximal portion of the main body circumferentially spaced a selected distance away from the release wire, and drawn tight and tied to itself to reduce the distal portion of the main body.

In one embodiment, the entry aperture opens into the main lumen.

In one embodiment, the entry aperture opens into the main lumen in a position proximal of the sealing portion.

In one embodiment, the entry aperture opens into the main lumen in a position within the sealing portion.

In one embodiment, the entry aperture opens distally in a position adjacent to the sealing stent.

In one embodiment, the wall comprises a closeable portion, the closeable portion adjacent to the distal sealing portion such that, in use, the closeable portion is closed by expansion of the distal sealing stent towards the lumen of the patient.

According to a second aspect of the invention, there is provided a stent graft assembly for placement in a lumen of a patient, the stent graft assembly comprising a stent graft and a pre-loaded guide wire, the stent graft comprising:
  a main tubular body of a biocompatible graft material having a main lumen, the main tubular body having a proximal end and a distal end;
  a side arm extending from the main tubular body, the side arm having a side arm lumen, the side arm lumen being in fluid communication with the main lumen through a side arm opening in the main tubular body; and
  a cannulation pocket, the pocket comprising:
    an exit aperture positioned opposite the side arm opening;
    an entry aperture longitudinally spaced from the exit aperture in a direction toward the distal end of the main tubular body; and a wall, the wall laterally spaced from the main lumen so as to provide a guide surface for a cannula fed through the entry aperture, wherein the pre-loaded guide wire comprises:

a first wire end projecting from the distal end of the main tubular body;

an intermediate wire portion extending through the entry aperture, the exit aperture and the side arm opening; and a second wire end projecting outwardly from the side arm.

In one embodiment, the side arm is angled with respect to the main tubular body such that the side arm lumen extends laterally and distally from the main lumen.

In one embodiment, the stent graft further comprises a central external zig-zag self-expanding stent which extends around both the main tubular body and a portion of the side arm, the central stent expandable so that the main lumen and the side arm lumen are each biased open allowing fluid to flow freely there-through.

In one embodiment, the stent graft further comprises a temporary diameter reduction constraint arrangement, the arrangement comprising:

a release wire; and a plurality of loops of thread, each loop engaged with the release wire and engaged around a proximal portion of the main body circumferentially spaced a selected distance away from the release wire, and drawn tight and tied to itself to reduce the distal portion of the main body.

BRIEF DESCRIPTION OF THE DRAWINGS

Embodiments of the present invention will be discussed with reference to the accompanying drawings wherein.

DETAILED DESCRIPTION OF THE DRAWINGS

Figure 1:
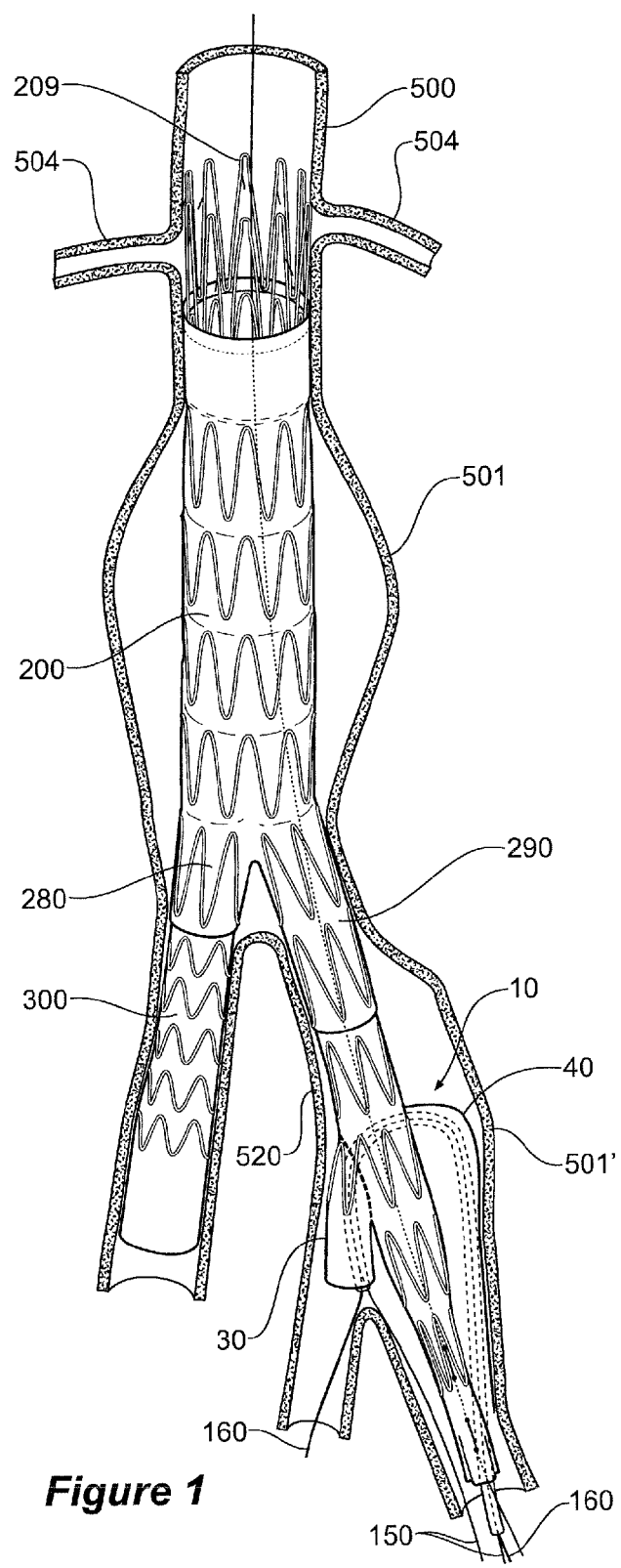
FIG. 1 is a diagrammatic view showing a cross section of the descending aorta, the aortic bifurcation and the common iliac arteries with a stent graft assembly according to the invention being deployed.

Referring to FIG. 1, the anatomy of a patient having an aneurysm 501 in the descending aorta and a further iliac aneurism 501' in the region of the common iliac artery 520. A first embodiment of the invention is shown in FIGS. 2a to 2d. This, and other embodiments of the invention, utilise the space created by the iliac aneurysm 501' to assist in cannulation as opposed to relying on the space within the lumen of the stent graft itself or access through the stent graft wall. As illustrated in FIG. 1, this allows for ipsilateral access for cannulation in stent grafts 10 with smaller diameters, rather than 'up and over' contralateral access.

Now referring to FIGS. 2a to 2d, a stent graft for placement in the lumen of a patient such as illustrated in FIG. 1, is shown. The stent graft 10 comprises a main tubular body 20 of a biocompatible graft material having a main lumen 22. A side arm 30 extends from the main tubular body 20. The side arm 30 has a side arm lumen 35, the side arm lumen 35 being in fluid communication with the main lumen 22 through a side arm opening 36 in the main lumen 22.

The side arm 30 is angled with respect to the main tubular body 20, such that the side arm lumen 35 extends laterally and distally from the main lumen 22. The stent graft 10 has a central external zig-zag self expanding stent 32, which extends around the main tubular body 20 and a portion of the side arm 30. The central stent 32 is expandable so that the main lumen 22 and the side arm lumen 35 are each biased open allowing fluid, typically blood, to flow freely therethrough.

Figure 2A:
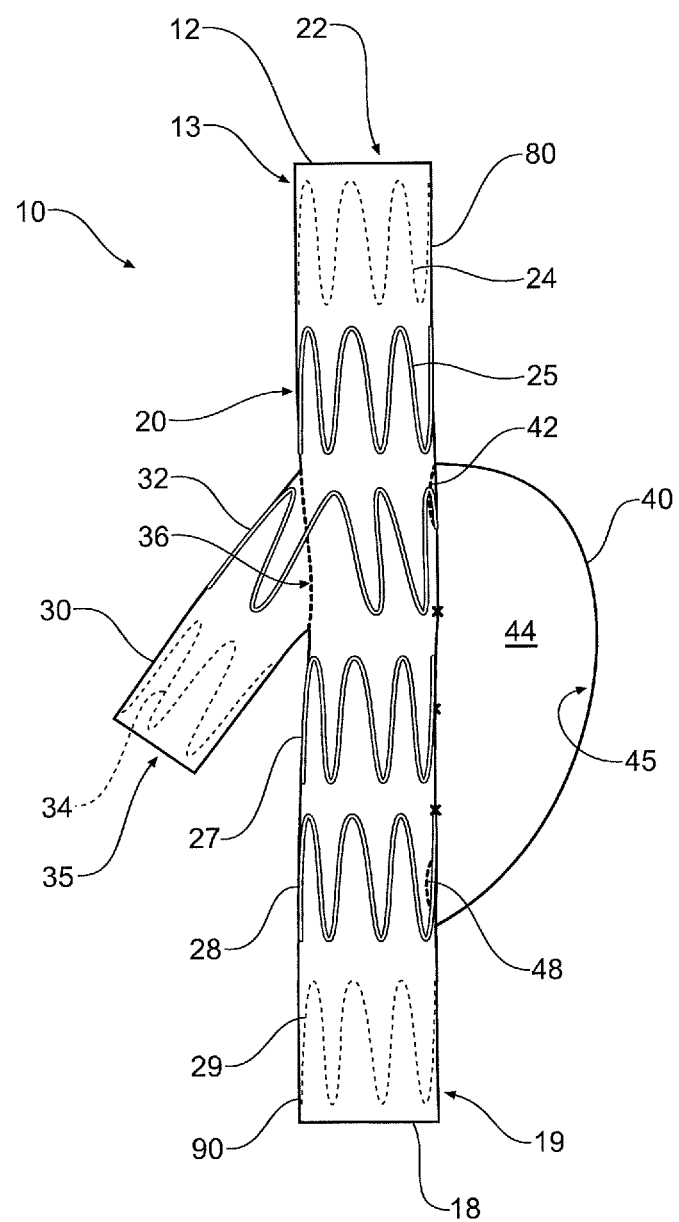
FIG. 2a shows the stent graft of FIG. 1 in a side view.

The stent graft 10 has a cannulation pocket 40, as is shown in FIG. 2a. The cannulation pocket 40 comprises an exit aperture 42 positioned opposite the side arm opening 36, an entry aperture 48 longitudinally spaced from the exit aperture 42 in a direction towards a distal end 18 of the main tubular body 20, and a wall 44, the wall 44 laterally spaced from the main lumen 22. The spacing of the lateral wall 44 from the main lumen 22 is such that a guide surface 45 is provided to guide a cannula or sheath 122 fed through the entry aperture 48 along a guide wire 150, as is shown in FIGS. 2c and 2d.

Again referring to FIG. 2a, it can be seen that the stent graft 10 comprises a distal sealing portion 90. The distal sealing portion 90 is sealable against the lumen of a patient, as is shown in FIG. 6c. The distal sealing portion 90 includes a distal sealing stent 29, the stent 29 expandable to seal the distal sealing portion 90 of the stent graft 10 against the lumen of the patient, as is shown in FIG. 6c.

Figure 2B:
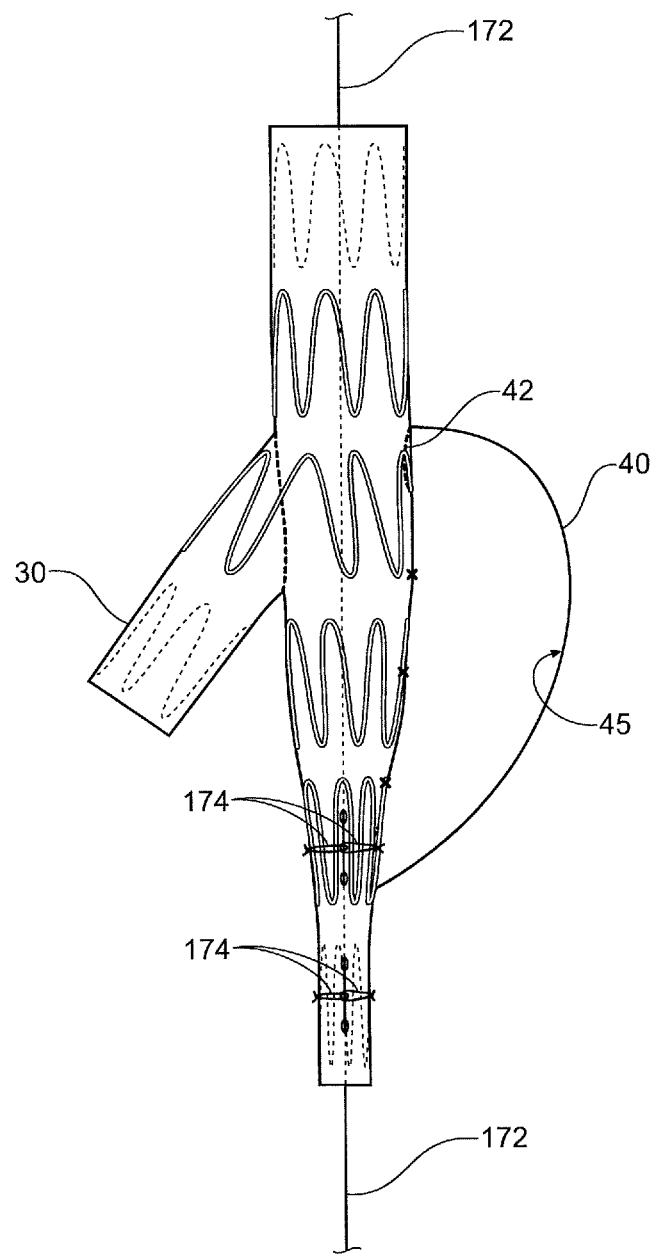
FIG. 2b is a similar view to FIG. 2a but shows the stent graft reduced using diameter reducing ties.
Figure 2C:
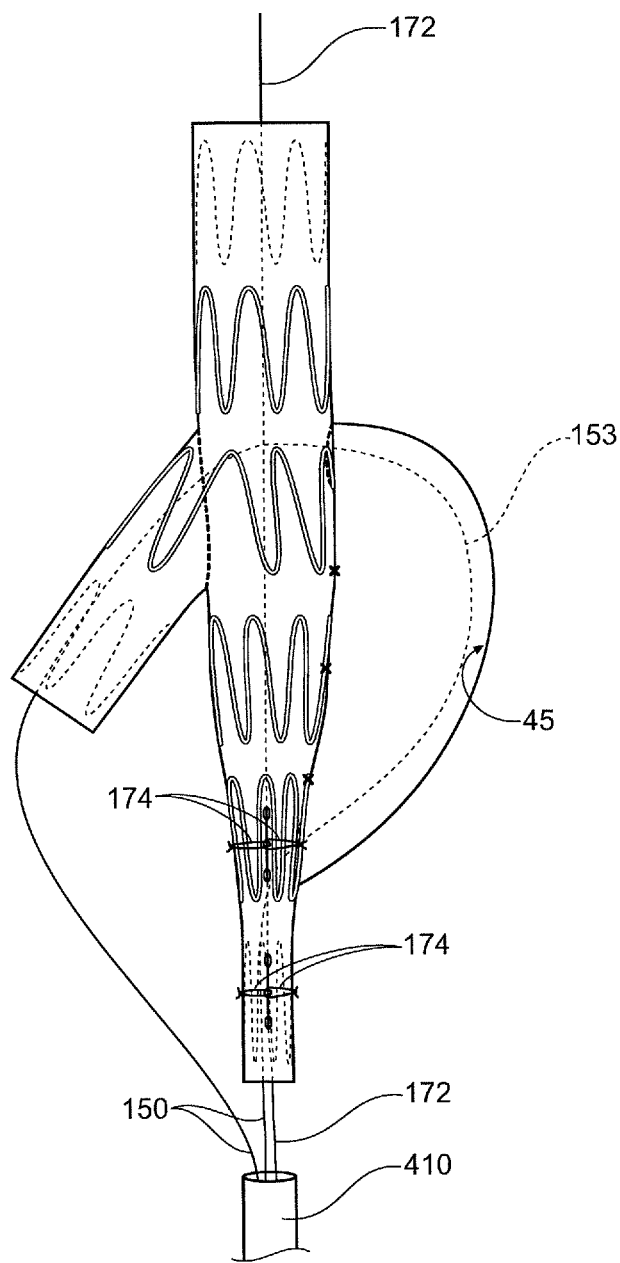
FIG. 2c is a similar view to FIG. 2b but shows the stent graft in combination with a guide wire.
Figure 2D:
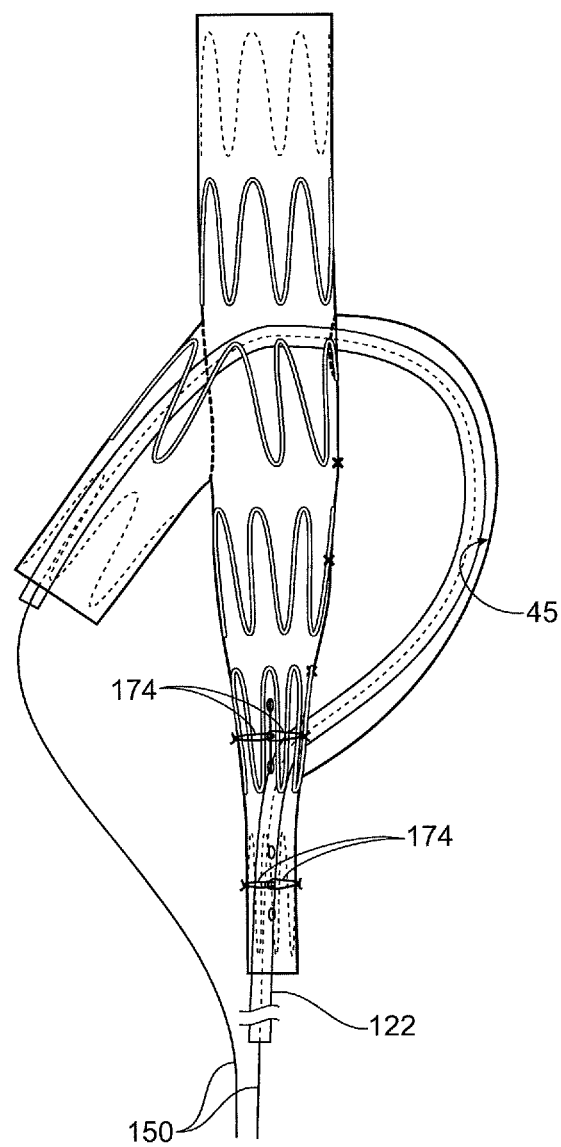
FIG. 2d is a similar view to FIG. 2c but shows in addition a sheath over the guide wire.

Now referring to FIG. 2b, the stent graft shown in FIG. 2a is shown reduced by a temporary diameter reduction constraint arrangement. The constraint arrangement comprises a release wire 172 and a plurality of loops of thread 174, each loop 174 engaged with the release wire 172 and engaged around a proximal portion of the main body 20 circumferentially spaced a selected distance away from the release wire 172, and drawn tight and tied to itself to reduce the distal portion 19 of the main body 20.

With the embodiment of the invention shown in FIGS. 2a through to 2d, the entry aperture 48 opens into the main lumen 22. More specifically, the entry aperture 48 opens into the main lumen 22 in a position proximal of the sealing portion 90.

Figure 3A:
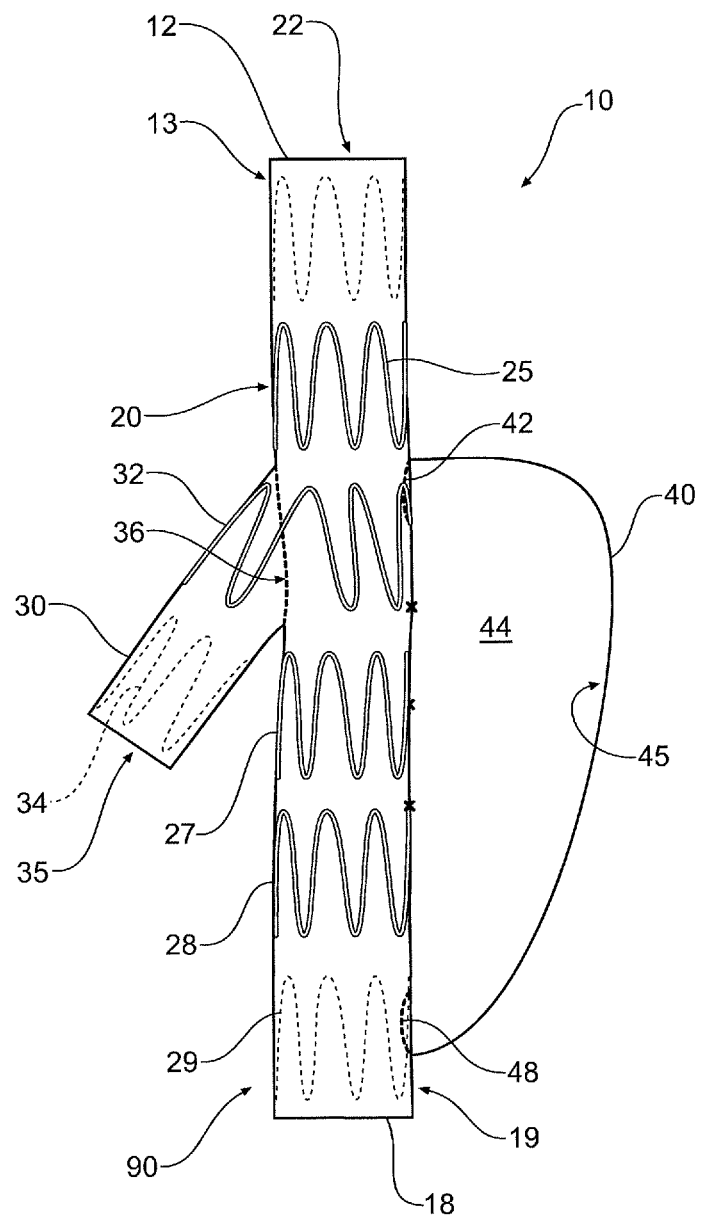
FIG. 3a shows an alternative stent graft to that shown in FIG. 1 in a side view.
Figure 3B:
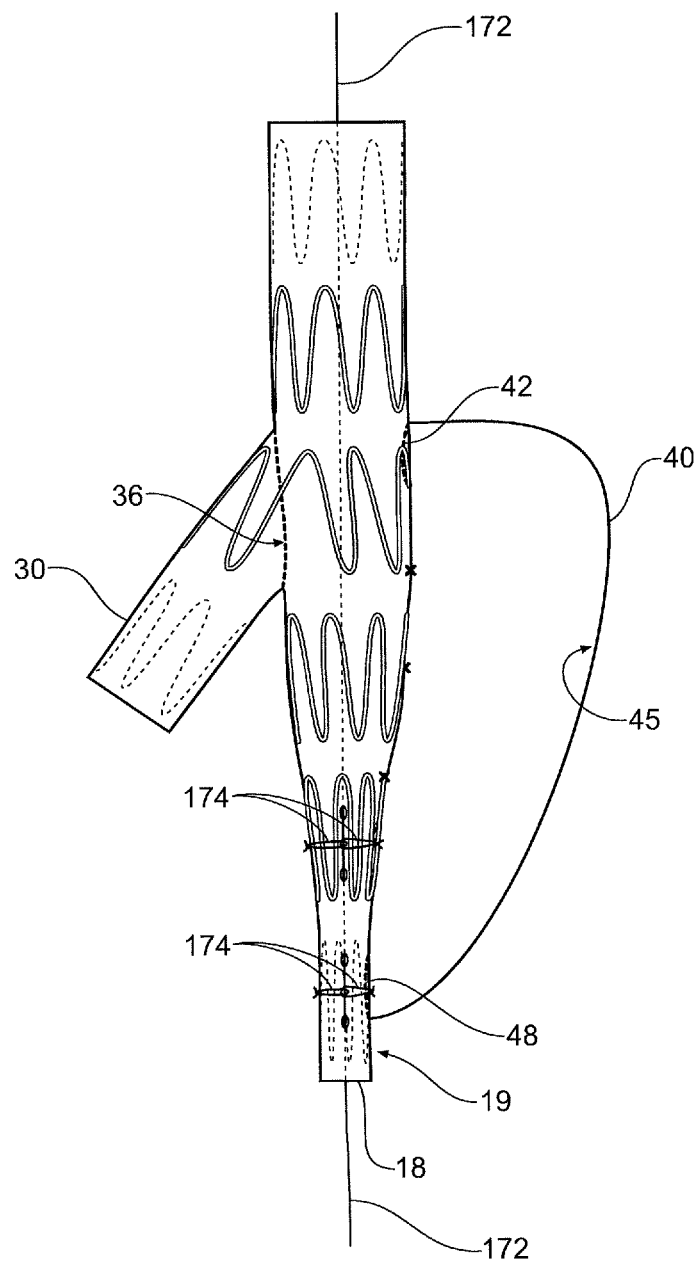
FIG. 3b is a similar view to FIG. 3a but shows the stent graft reduced using diameter reducing ties.
Figure 3C:
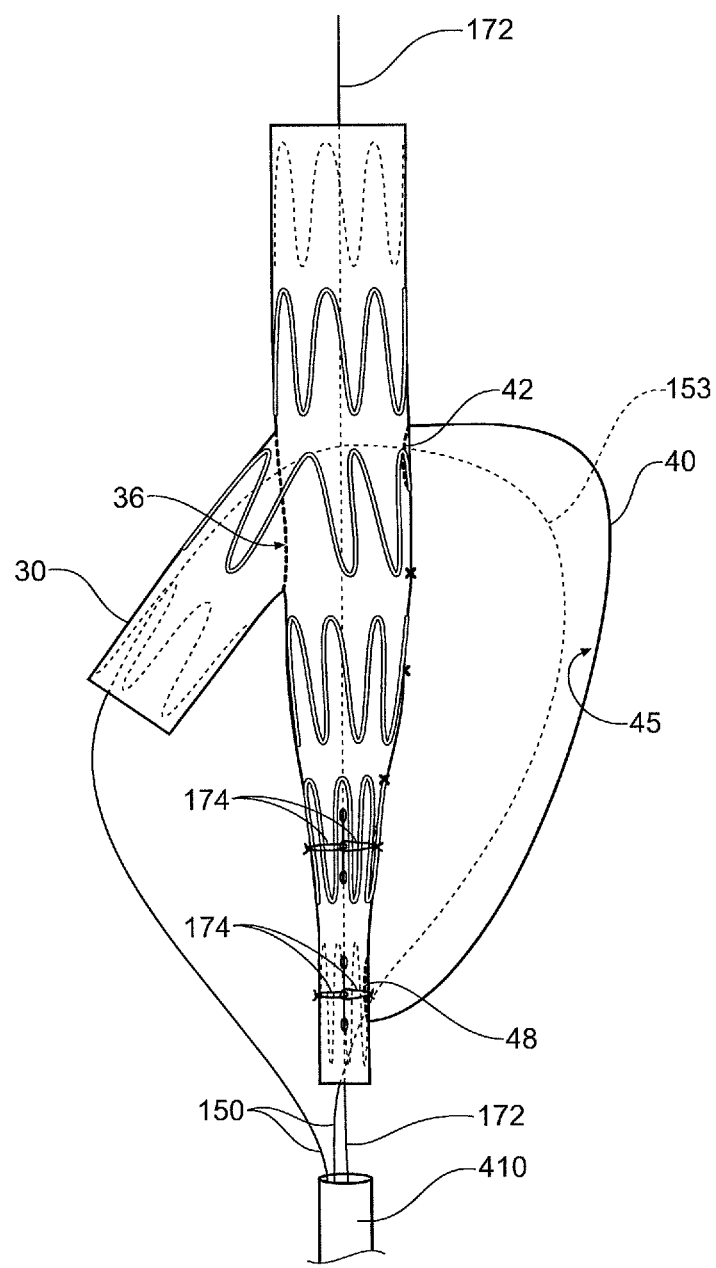
FIG. 3c is a similar view to FIG. 3b but shows the stent graft in combination with a guide wire.

Referring now to FIGS. 3a, 3b and 3c, a second embodiment of the invention is shown. This embodiment of the invention is similar to the embodiment of the invention shown in FIGS. 2a to 2d, however the entry aperture 48 opens into the main lumen 22 in a position within the sealing portion 90.

Figure 4A:
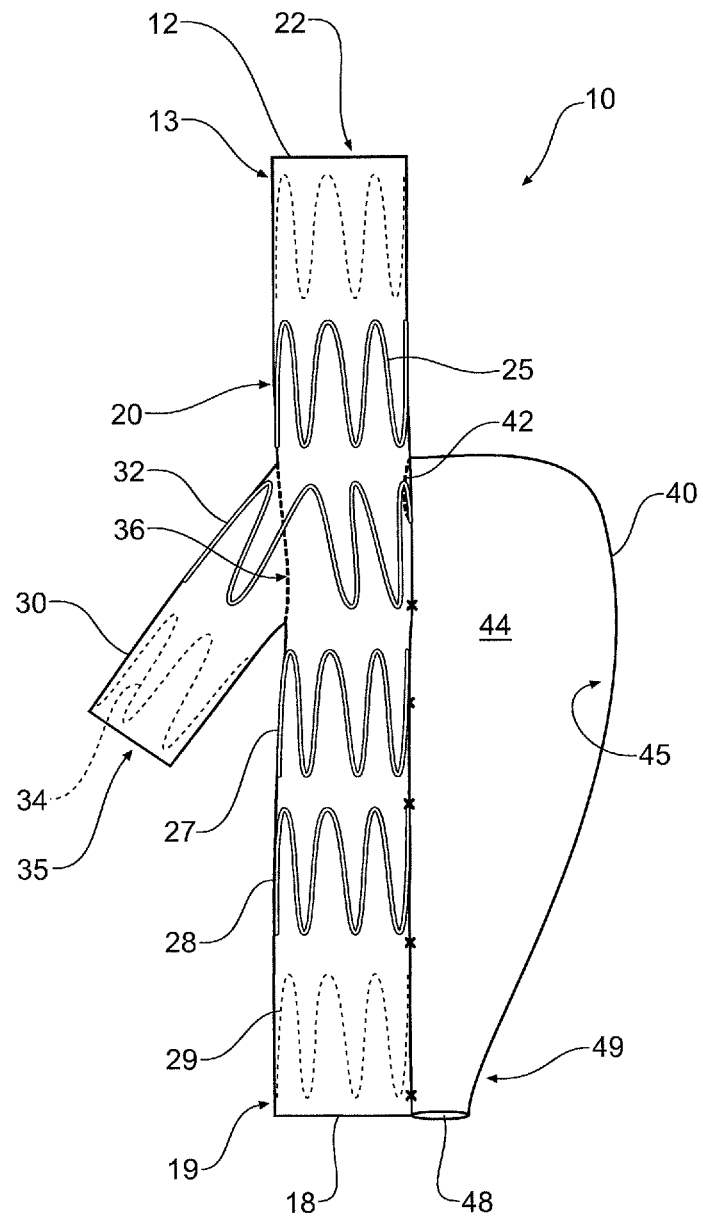
FIG. 4a shows an alternative stent graft to that shown in FIG. 1 in a side view.
Figure 4B:
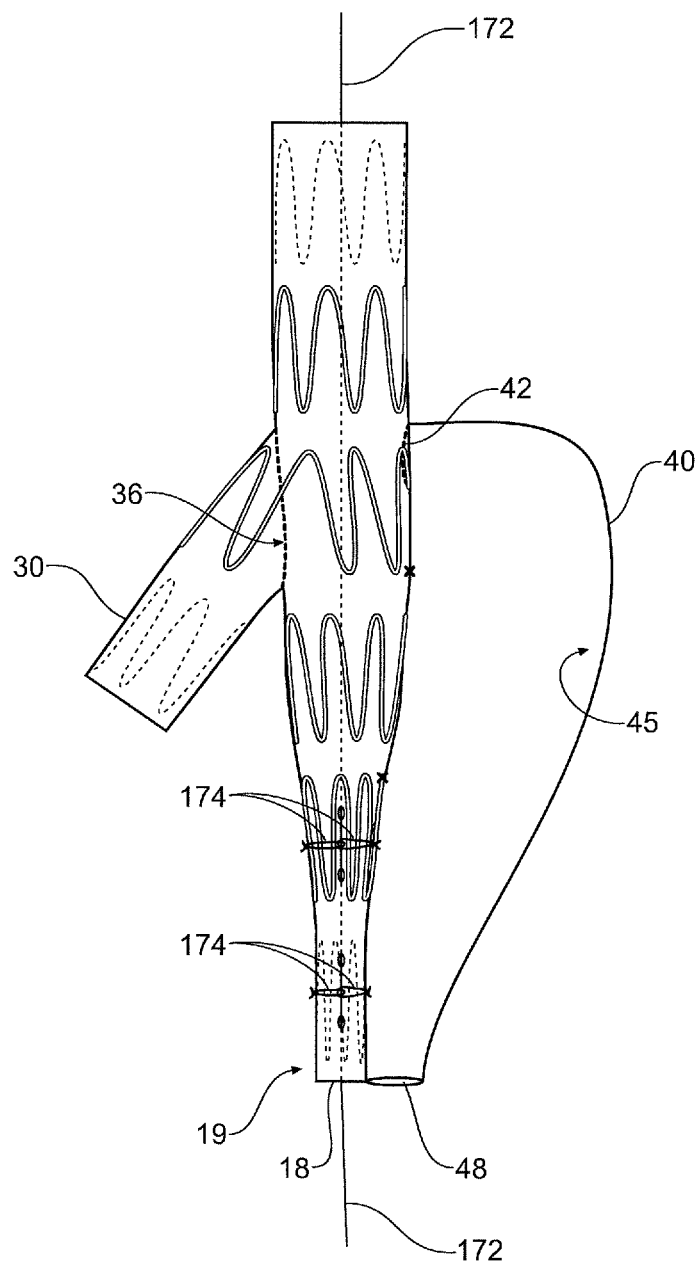
FIG. 4b is a similar view to FIG. 4a but shows the stent graft reduced using diameter reducing ties.
Figure 4C:
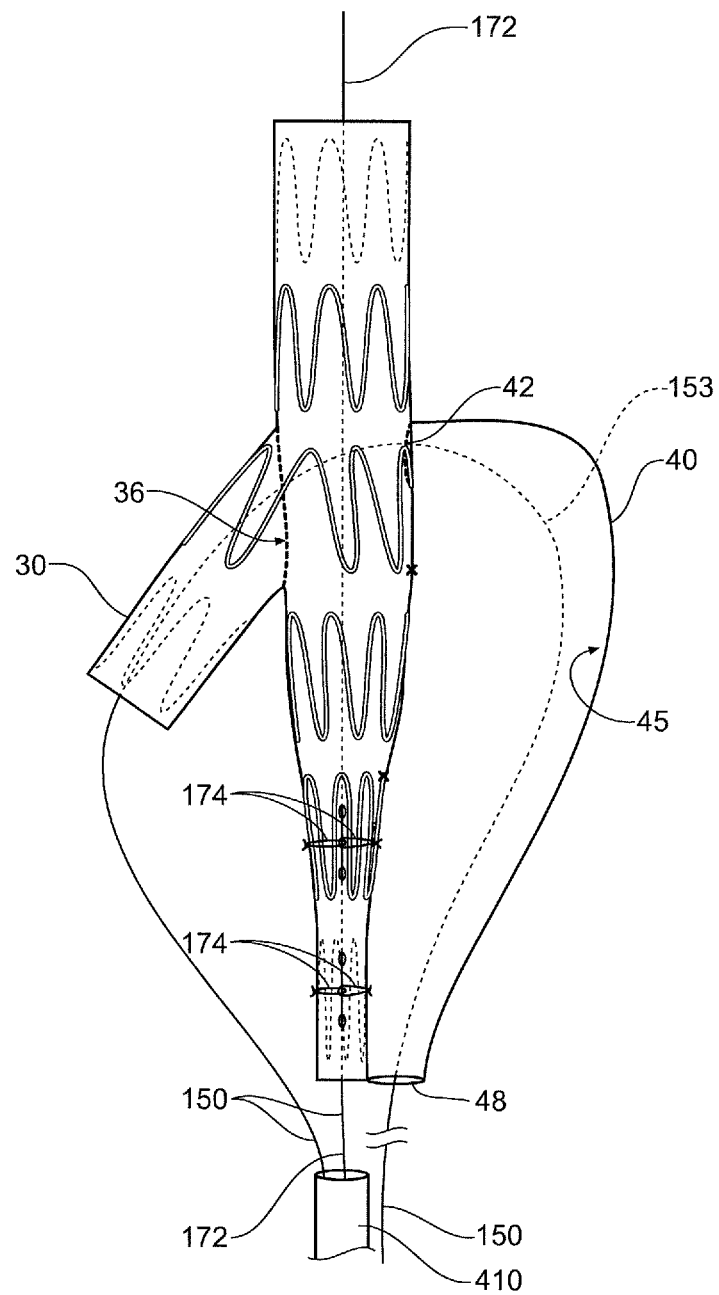
FIG. 4c is a similar view to FIG. 4b but shows the stent graft in combination with a guide wire.

Referring now to FIGS. 4a to 4c, a third embodiment of the invention is shown. With this embodiment of the invention, the stent graft 10 includes an entry aperture 48 that opens distally in a position adjacent to the sealing stent 29. The wall 44 comprises a closable portion 49.

Figure 7:
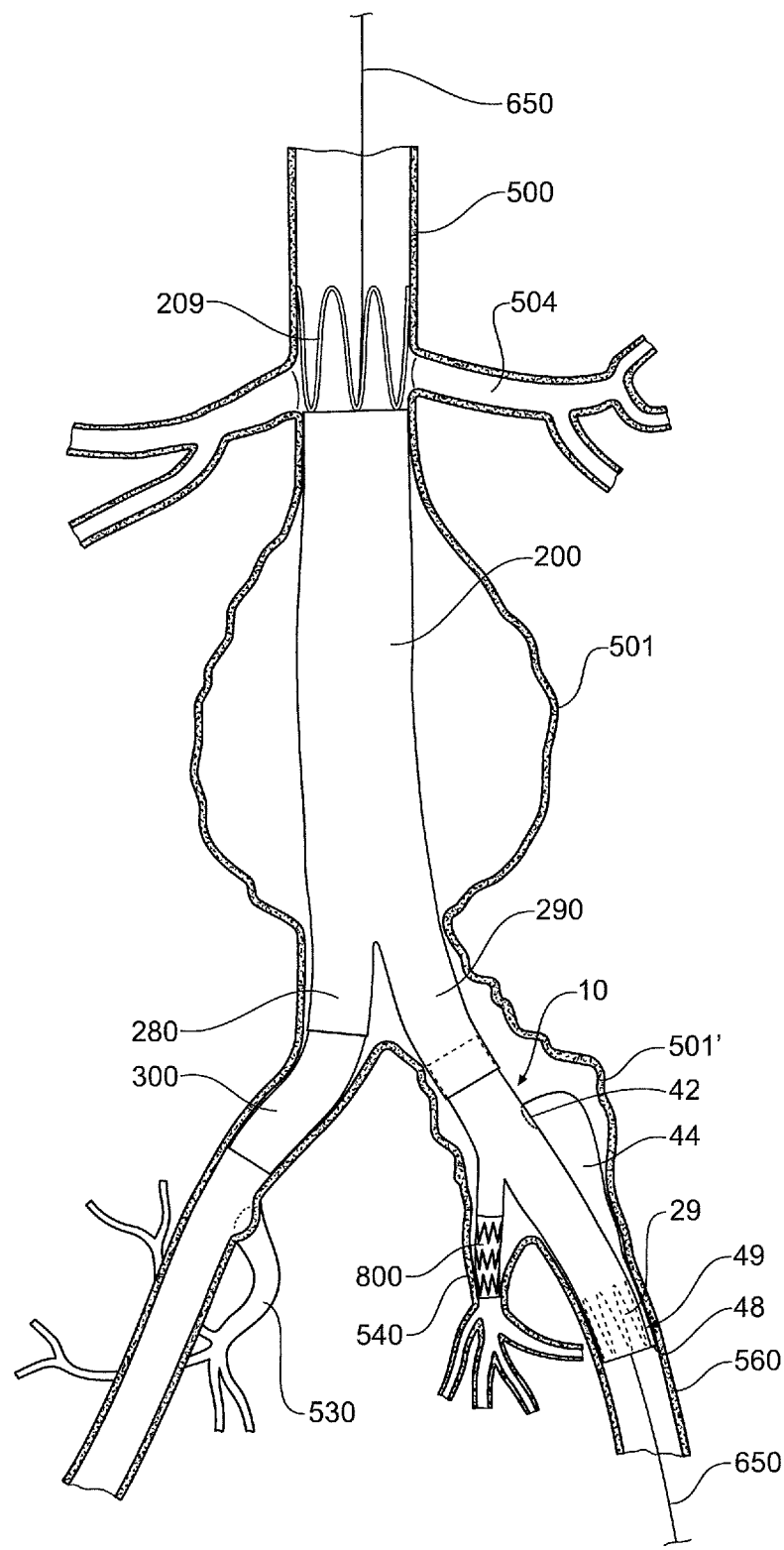
FIG. 7 is a similar view to FIG. 5h but shows the stent graft of FIGS. 4a to 4c as deployed within the vascular system of a patient.

The closable portion 49 is adjacent to the distal sealing portion 19 such that, in use, the closable portion 49 is closed by expansion of the distal sealing stent 29 towards the lumen of the patient. This closed position is shown in FIG. 7.

Referring to FIGS. 2c, 3c and 4c, a guide wire 150 is shown. This guide wire can be introduced during deployment of the stent graft 10, or advantageously, can be pre-loaded through a sheath 410 of a delivery device 400. U.S. Patent Application Publication No. 2012/0041535 A1 describes a pre-loading method and a method of cannulating fenestrations that can be used with the stent graft described in the present application. This patent reference is incorporated by reference herein in its entirety.

The pre-loaded wire 150, shown in FIGS. 2c, 3c and 4c, has a first wire end 151 projecting from the distal end 18 of the main tubular body 20, an intermediate wire portion 153 extending through the entry aperture 48, the exit aperture 42 and the side arm opening 36; and a second wire end 152 projecting outwardly from the side arm opening 36. The ends 151 and 152 are shown in FIG. 5e.

Referring now to FIGS. 5a to 5j, deployment of a stent graft according to the second embodiment of the invention shown in FIGS. 3a to 3c will now be described.

This description will also be applicable to other embodiments of the invention, such as the first and third embodiments described with reference to FIGS. 2a to 2d and FIGS. 4a to 4c respectively.

Figure 5A:
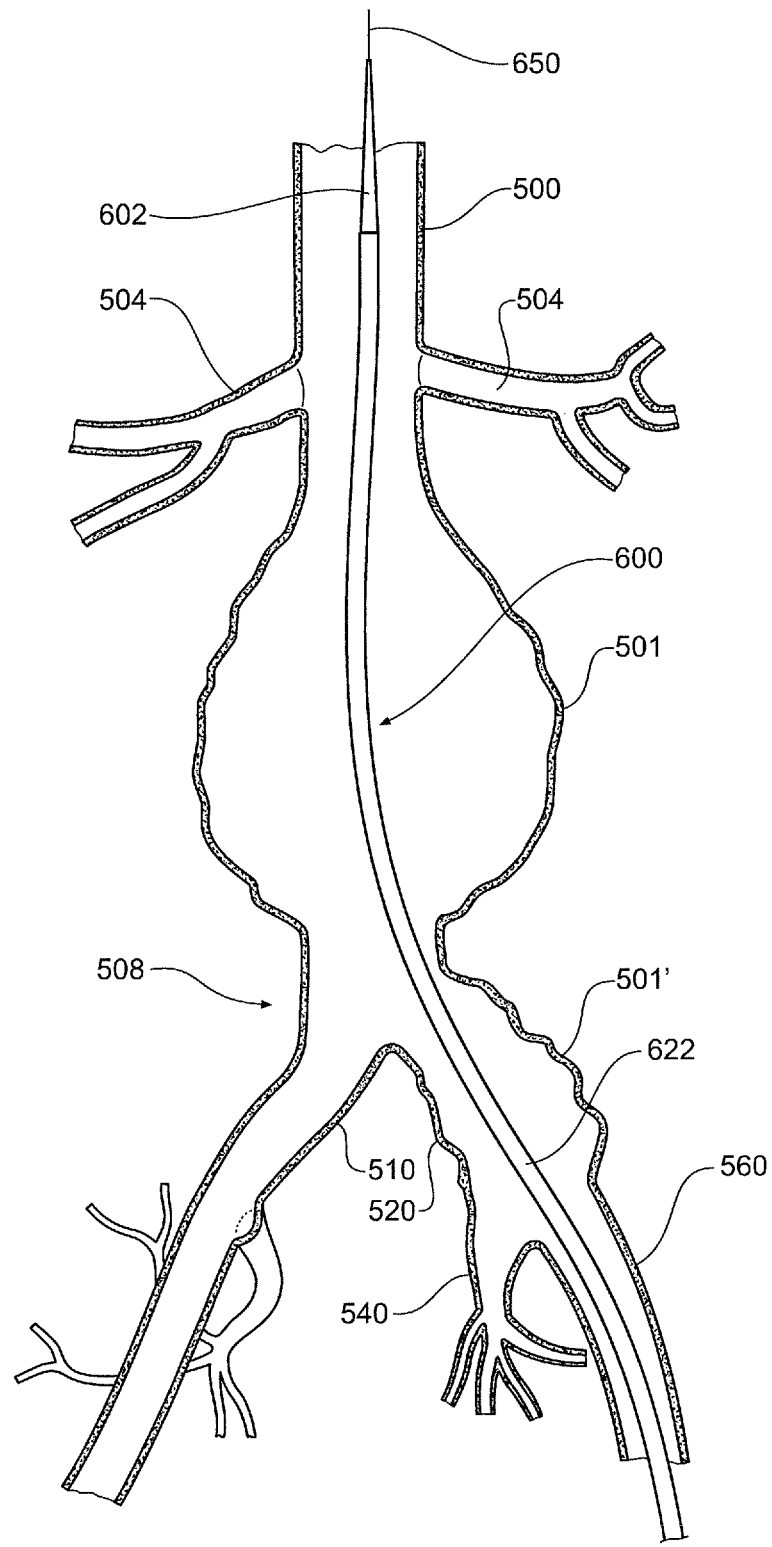
FIGS. 5a to 5j show the various stages of deployment of a stent graft, such as the stent graft shown in FIGS. 3a to 3c, into the vascular system of the patient.

FIG. 5a shows a schematic vascular of a patient, including an aorta 500, renal arteries 504 and aortic bifurcation 508. Extending from the aortic bifurcation 508 are iliac arteries 510 and 520. The aorta has an aneurysm 504', which extends down the common iliac artery to the position of the internal iliac artery 540. The iliac bifurcation is the bifurcation between the internal iliac artery 540 and the external iliac artery 560.

Referring first to FIG. 5a, a delivery device 600 with a nose cone dilating tip 602 is shown. The tip 602 is shown proximal of the renal arteries 504 on a guide wire 650. The process of getting the delivery device 600 into this position, using the guide wire 650, is currently known in the art.

Figure 5B:
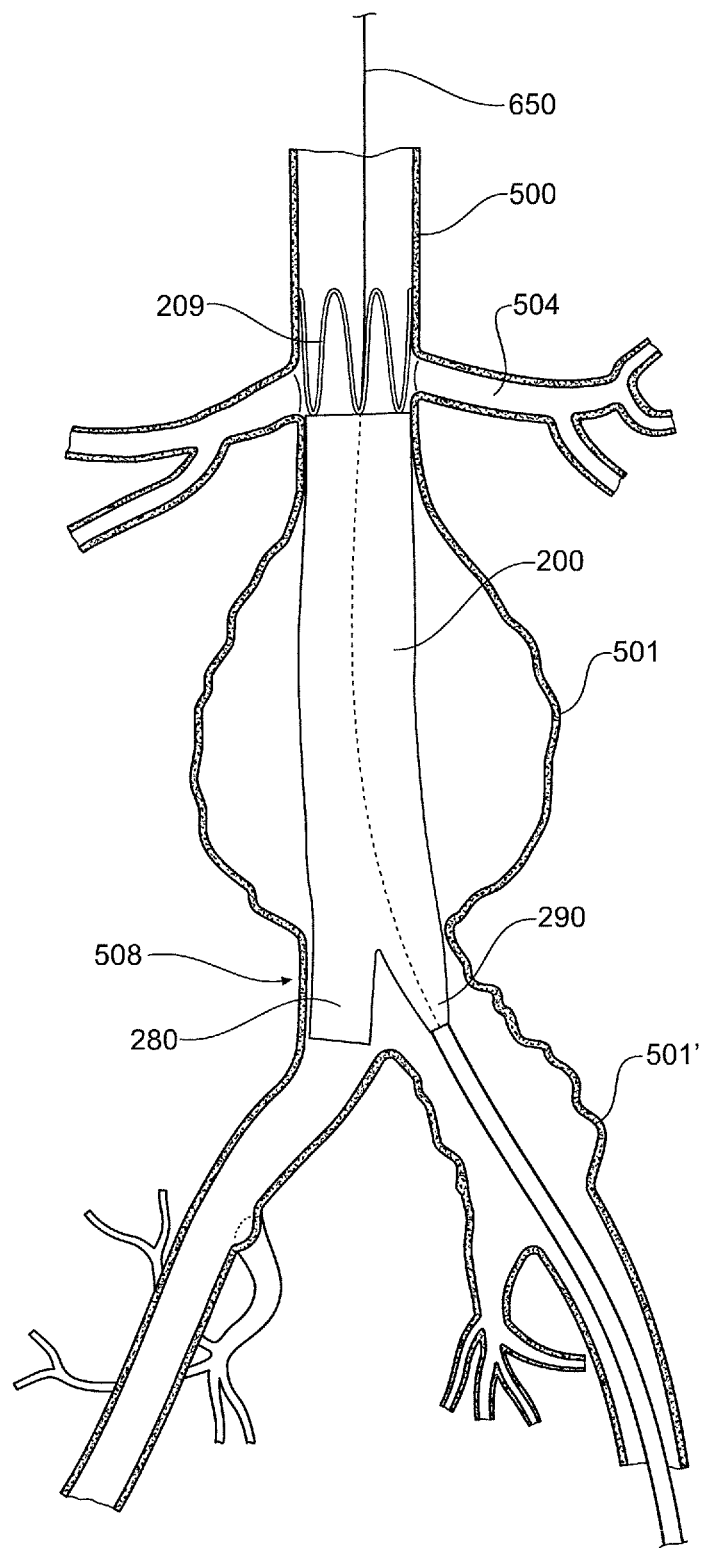

Turning to FIG. 5b, deployment of a suprarenal stent graft 200 is shown. The suprarenal stent graft 200 has an exposed stent 209 to allow perfusion of the renal arteries 504. The suprarenal stent graft 200 also has a prosthetic trunk 280 for the contralateral side of the aortic bifurcation 508 and a prosthetic trunk 290 for the ipsilateral side of the aortic bifurcation 508.

Figure 5C:
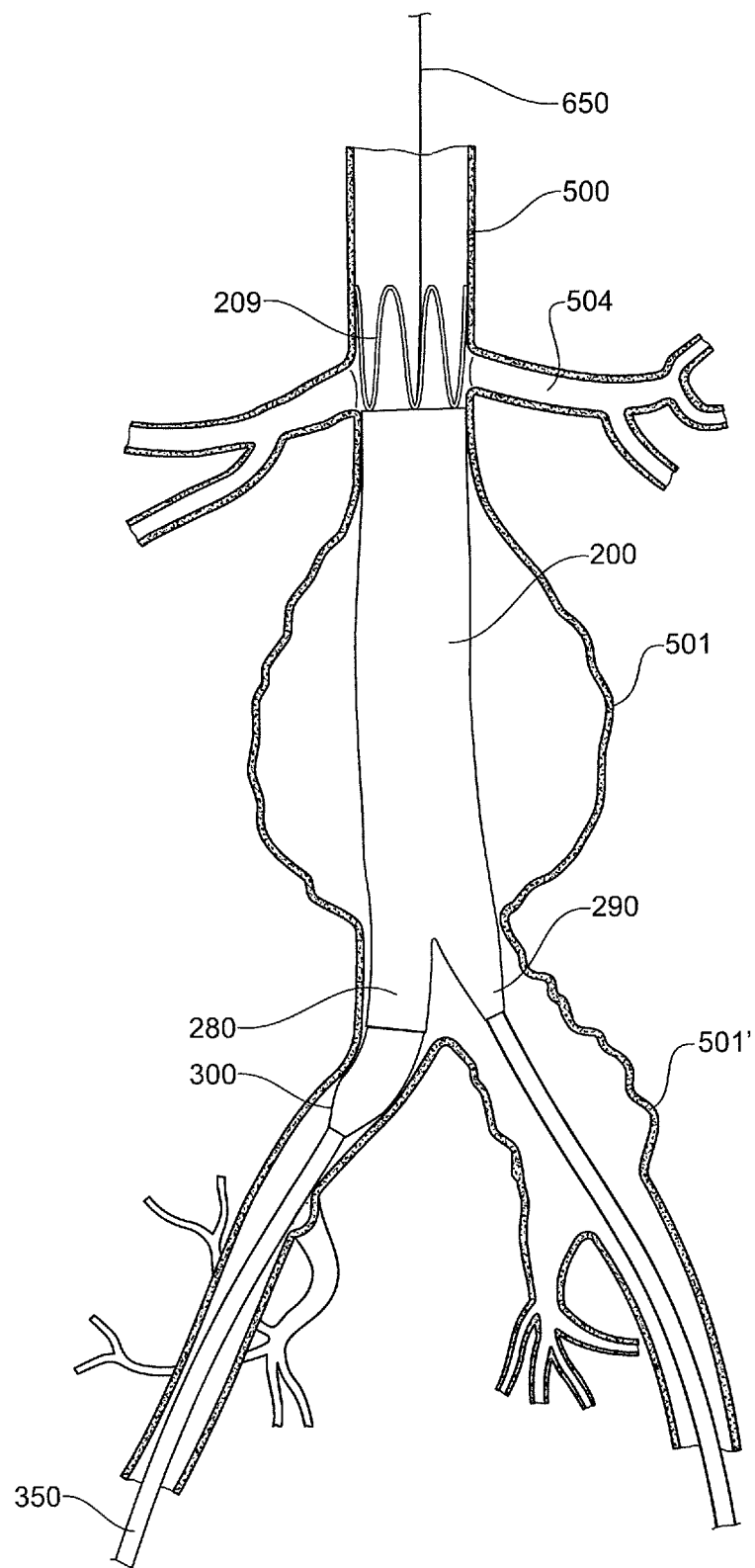

FIG. 5c shows the deployment of a common iliac leg extension piece 300, as is known in the art.

Figure 5D:
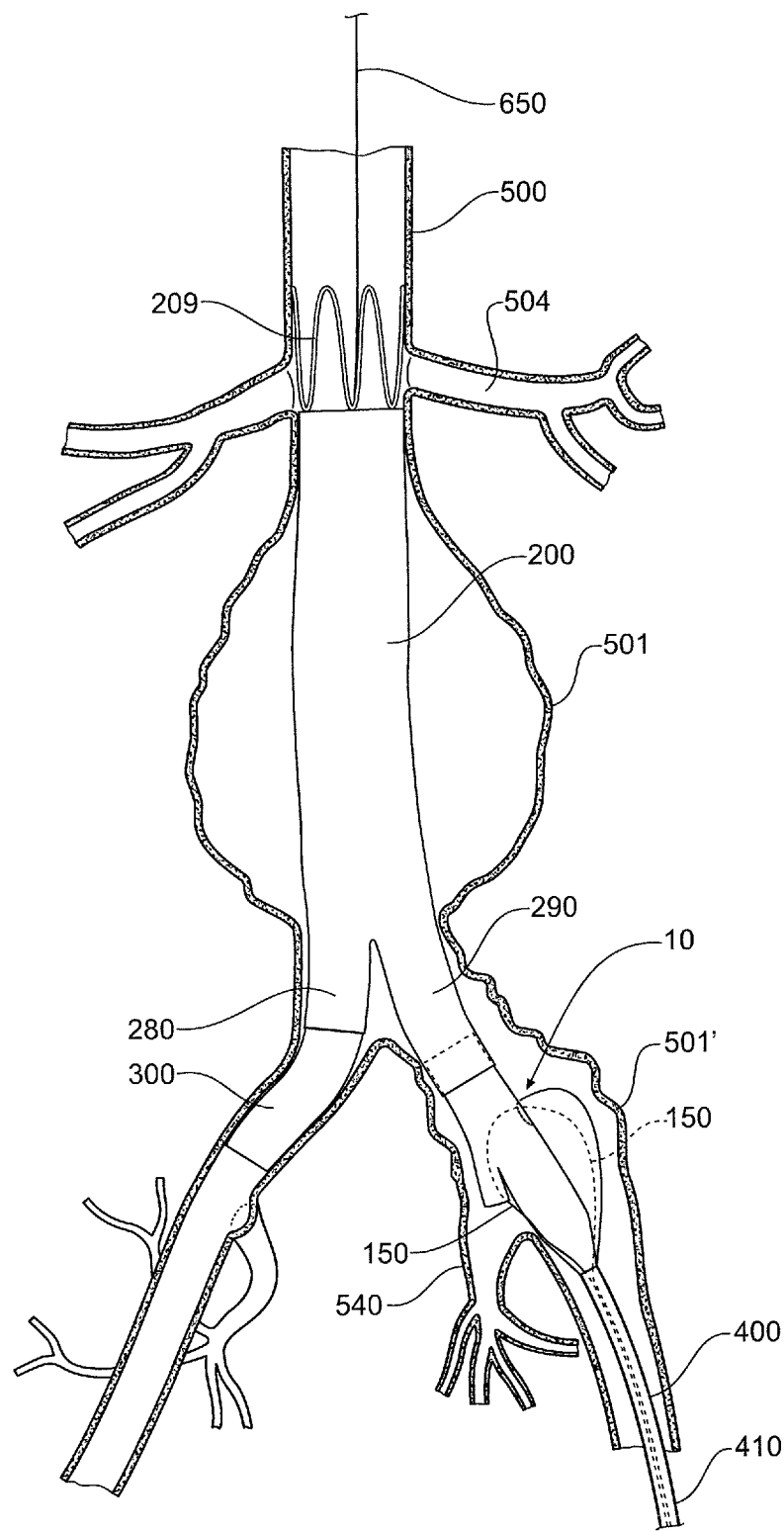
Figure 5E:
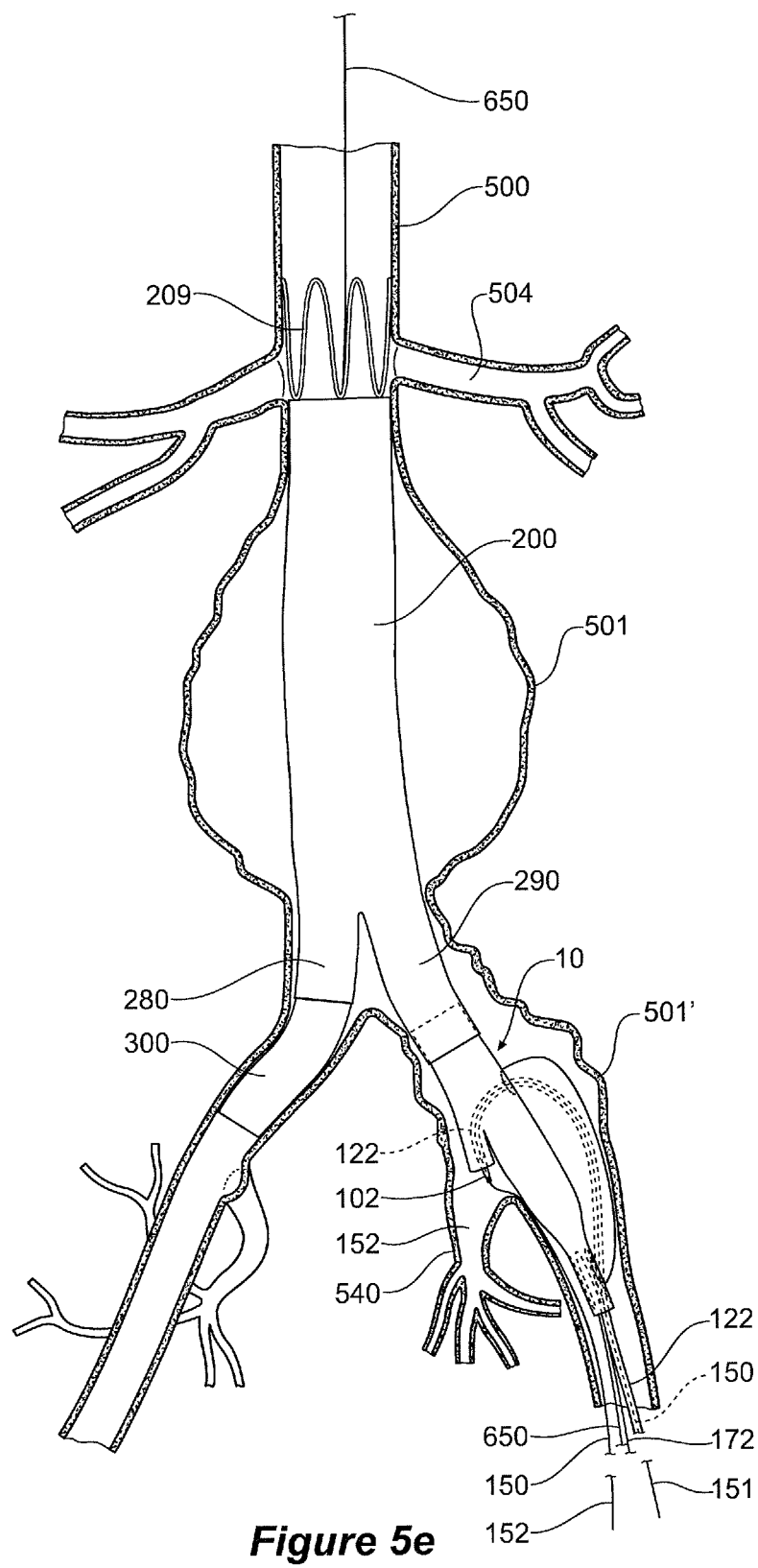

FIG. 5d shows a stent graft 10 according to the second embodiment of the invention, as illustrated in FIGS. 3a to 3c, being deployed from a further delivery device 400. This delivery device 400 is pre-loaded with a guide wire 150. From this position, the sheath 410 of the delivery device 400 is further retracted and then removed, as is shown in FIG. 5e.

FIG. 5e shows sheath 122 having a tip 102 advanced over the pre-loaded guide wire 150 towards the internal iliac artery 540. At this point, the diameter reducing ties, shown more clearly in FIG. 3b, are still in place.

Figure 5F:
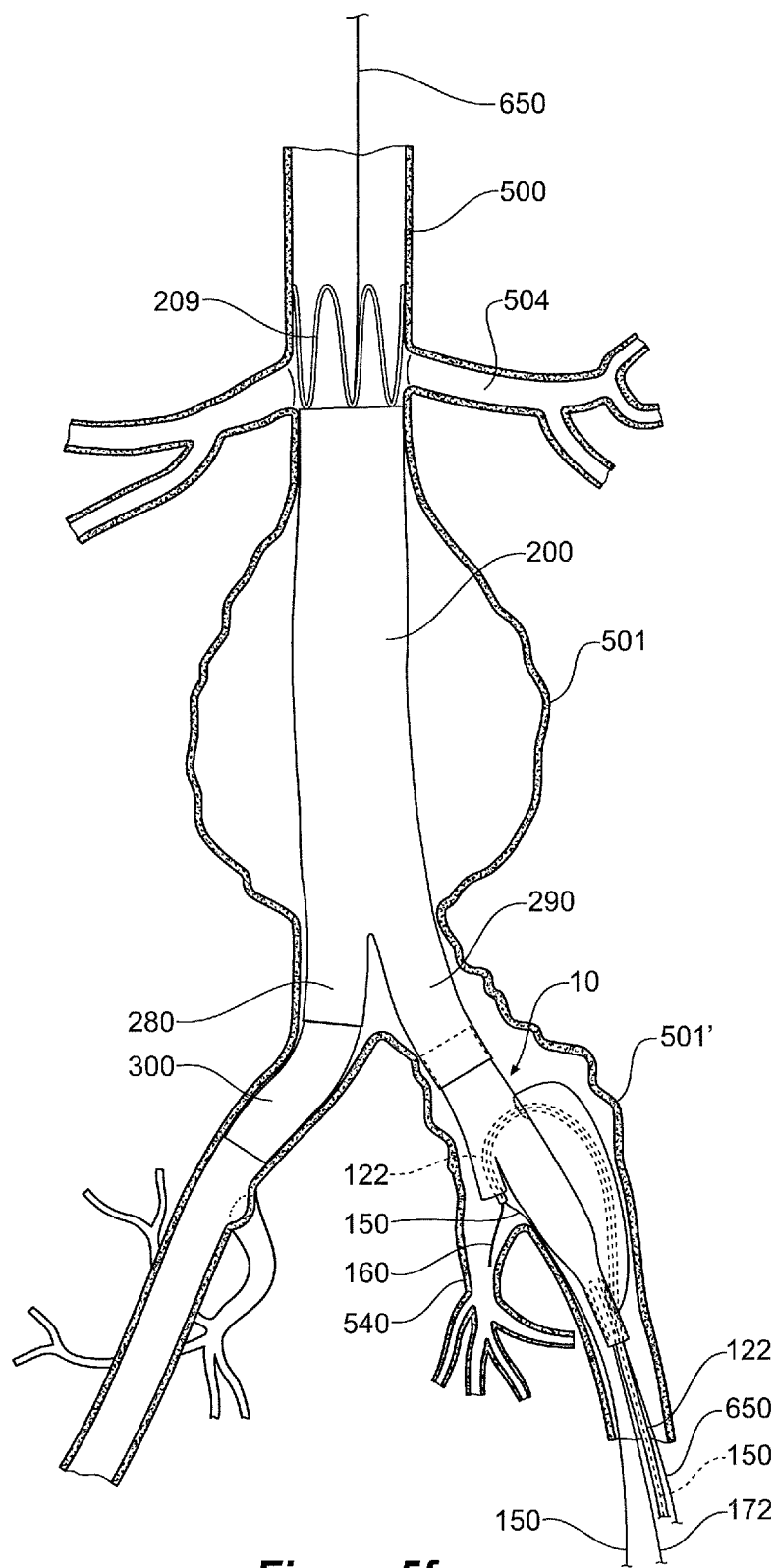

Turning now to FIG. 5f, the tip 102 has been retracted and a further guide wire 160 is deployed through the sheath 122 such that it extends down into the internal iliac artery 540 (the guide wire 160 can be pierced into the sheath 122 or can enter the sheath 122 through porting in a handle for instance).

Figure 5G:
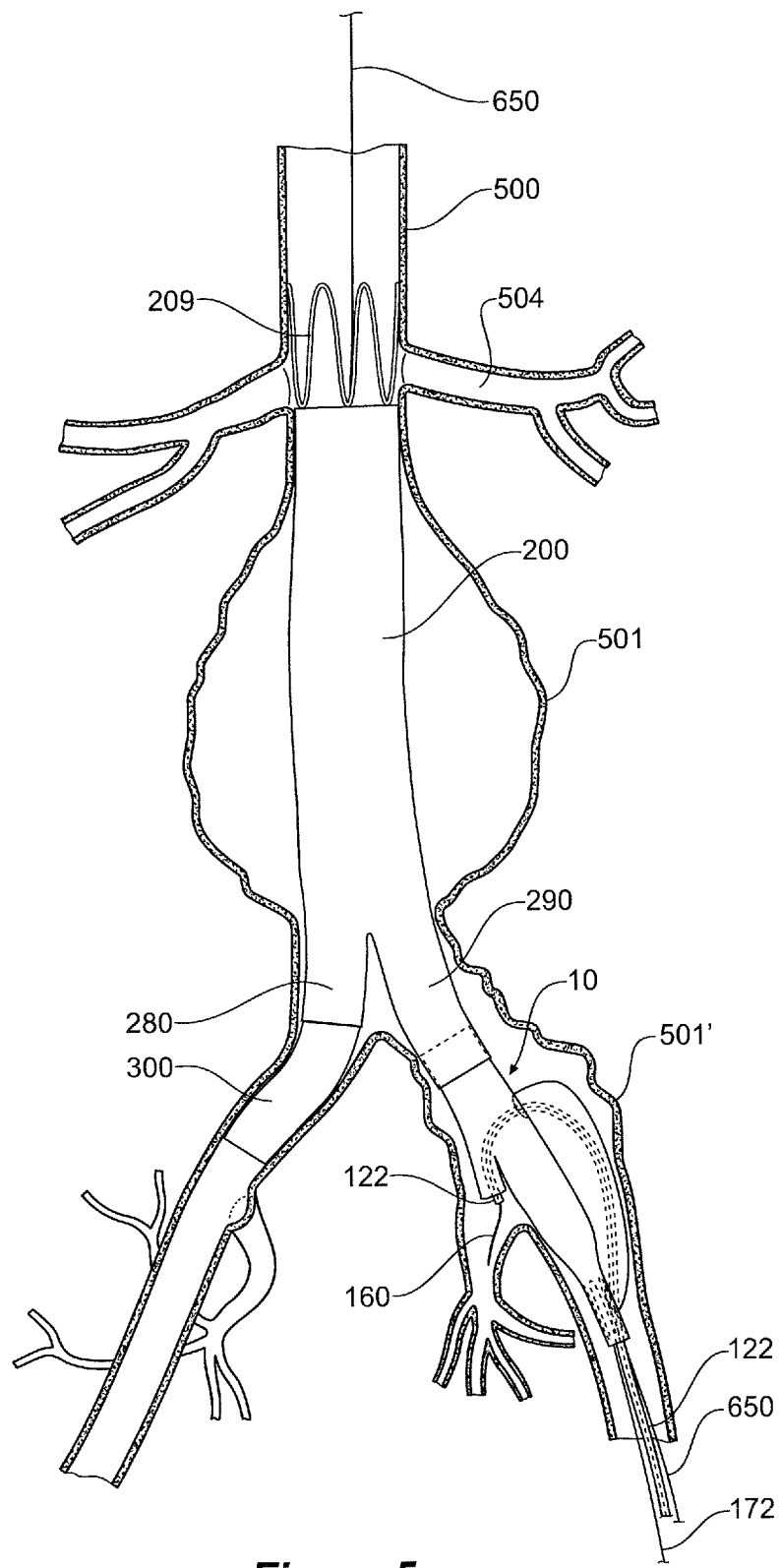

Next, the pre-loaded guide wire 150 is removed, as is shown in FIG. 5g. This allows the sheath 122 to be pushed over the further wire 160 that has cannulated the internal iliac artery 530, so as to be ready for a smaller internal iliac leg extension stent 800 to be tracked through the sheath 122 and deployed into the internal iliac artery.

Figure 5H:
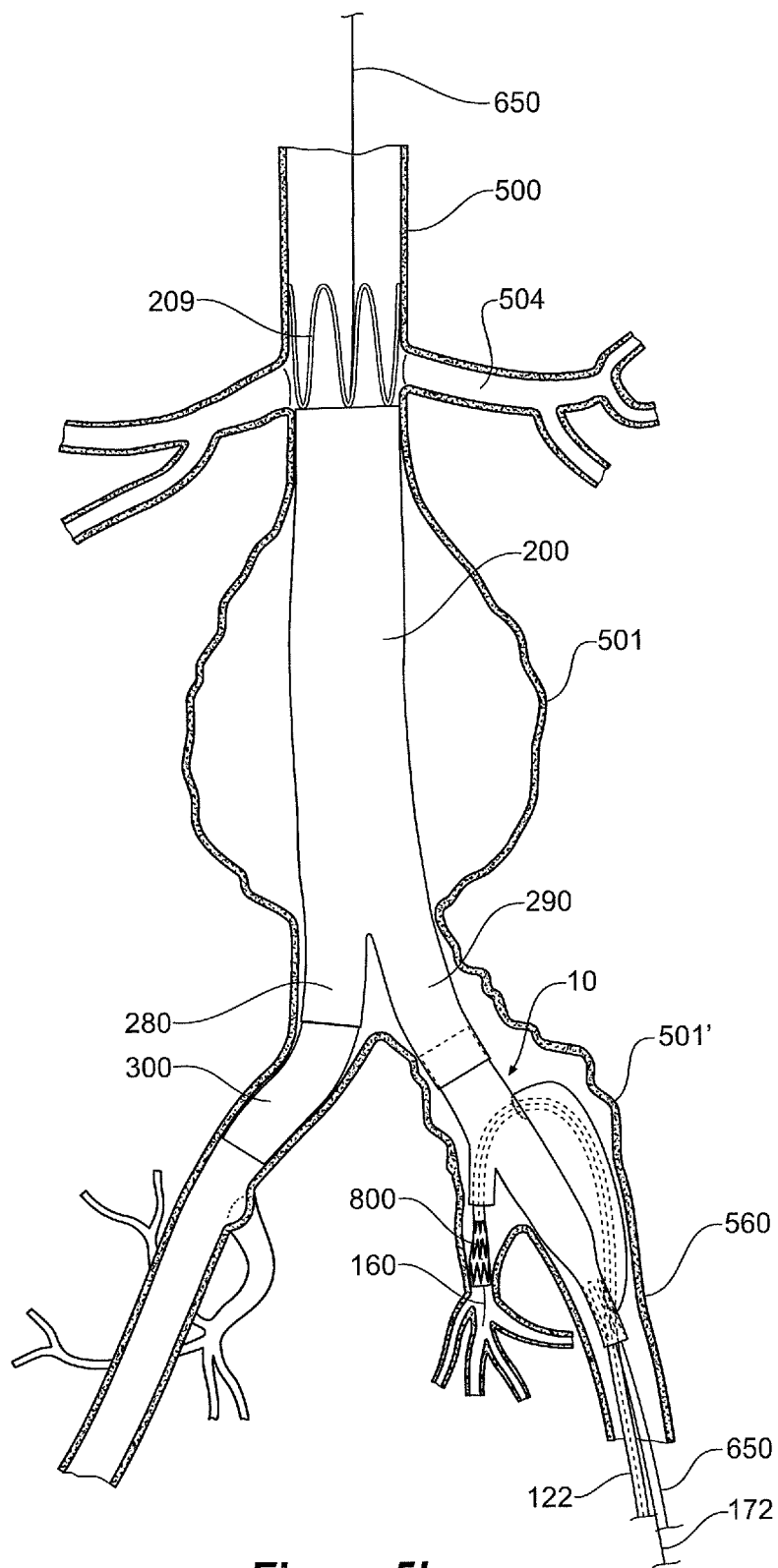
Figure 5I:
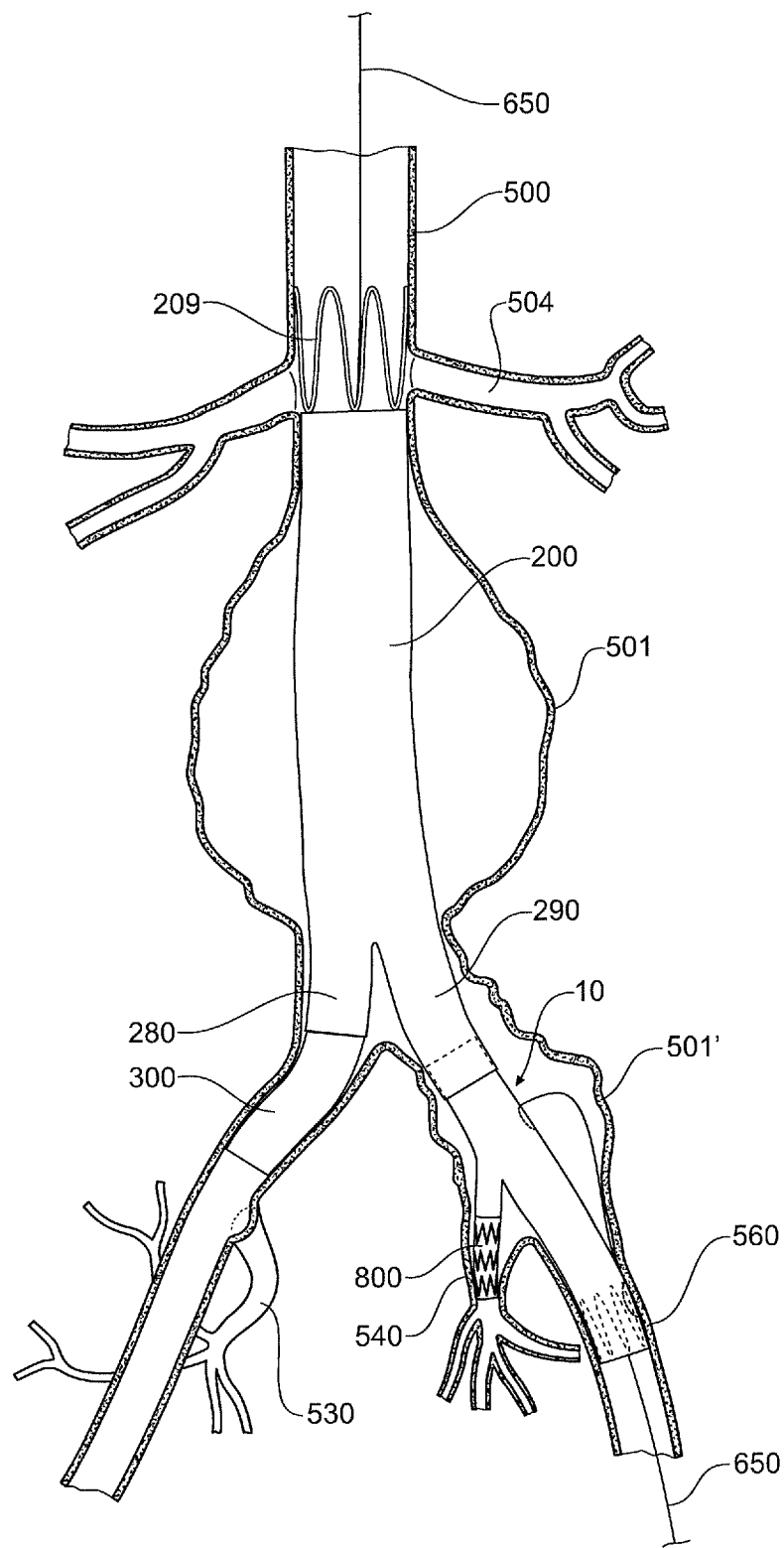

The deployment of the internal iliac leg extension 800 is shown sequentially in FIGS. 5h to 5i.

FIG. 5i shows the diameter reducing ties 174 having been removed through retraction of the diameter reducing tie release 172. This allows the sealing stent 29 (shown in FIG. 2a) to expand, thereby sealing the distal sealing portion 90 of the stent graft 10 against the wall of the external iliac artery 560. This also has the effect of closing off the entry aperture 48 leading into the cannulation pocket 40.

Figure 5J:
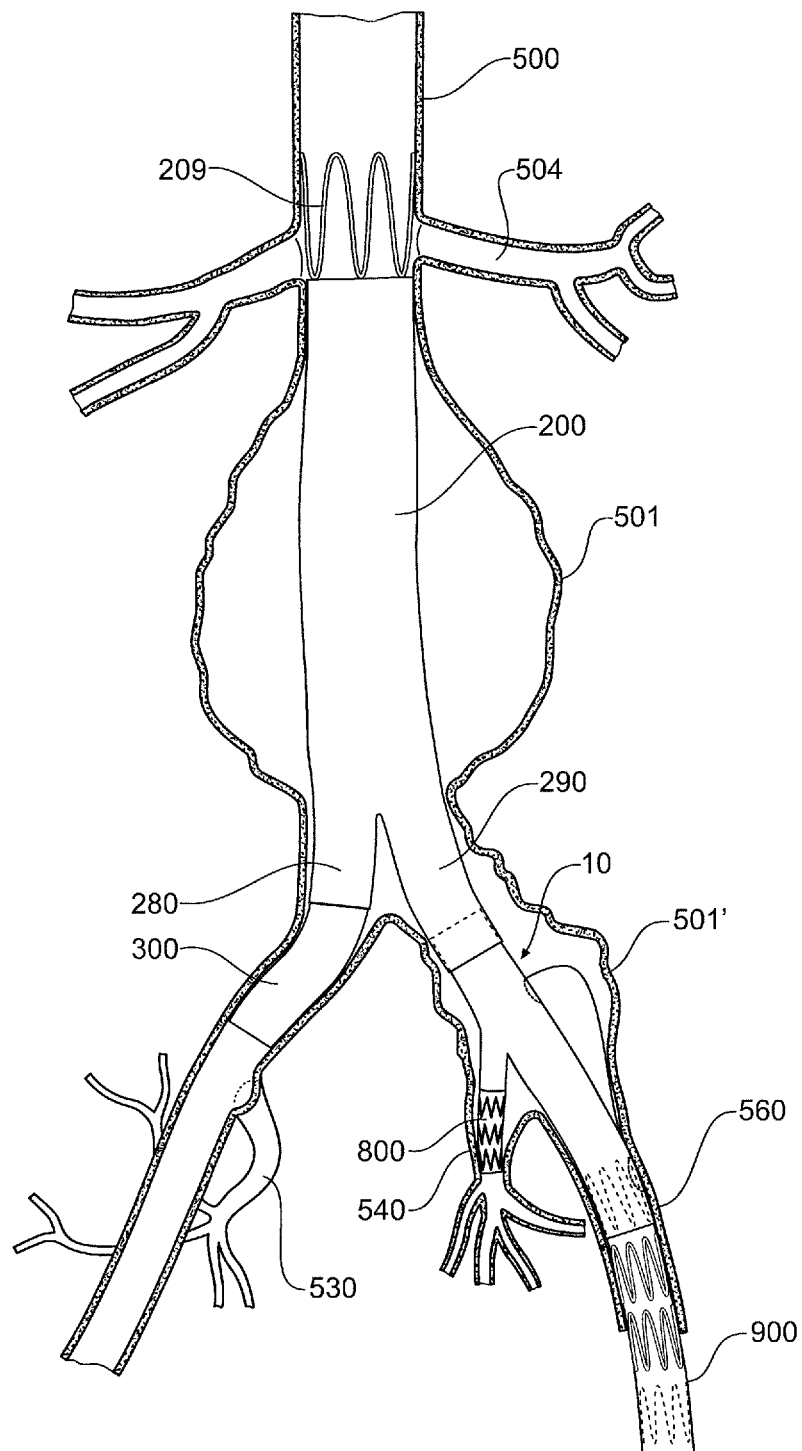

FIG. 5j shows an internal iliac extension piece 900 having been deployed. In some instances, depending on the size and shape of the aneurysm 501', this further extension piece 900 may not be required.

Figure 6A:
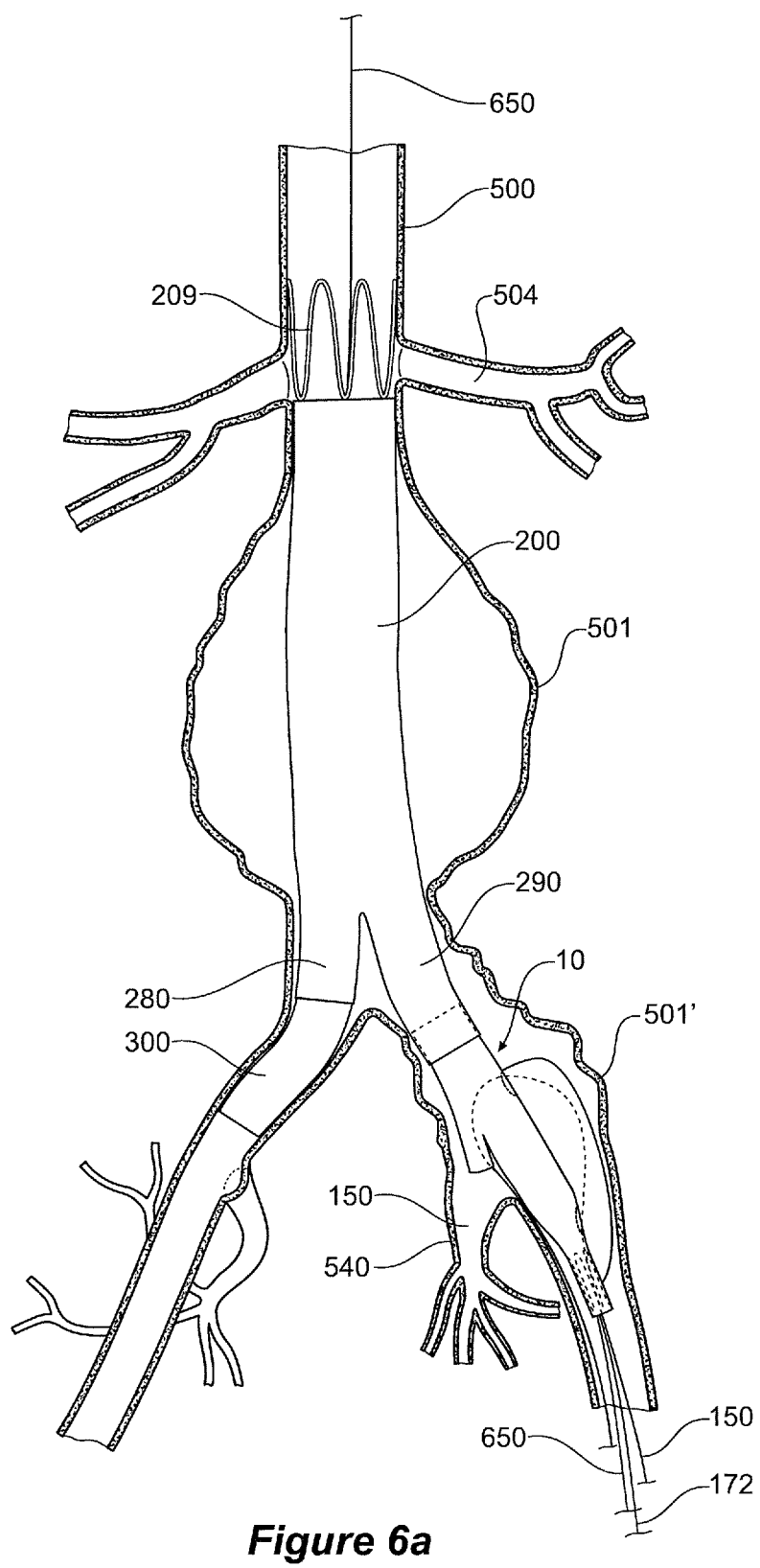
FIGS. 6a, 6b and 6c are similar to FIGS. 5e, 5f and 5i but show deployment of a stent graft as illustrated in FIGS. 2a to 2d.
Figure 6B:
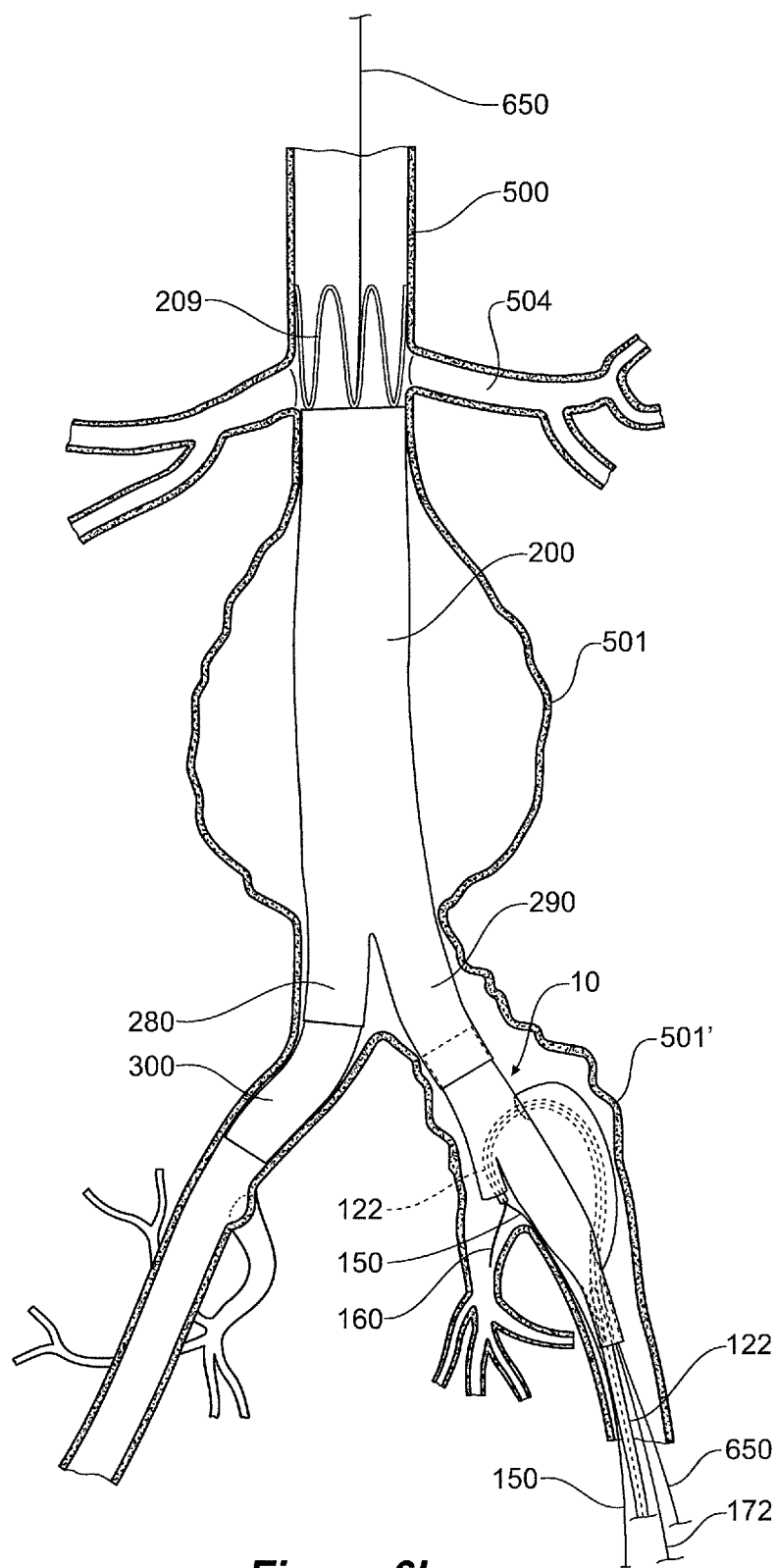
Figure 6C:
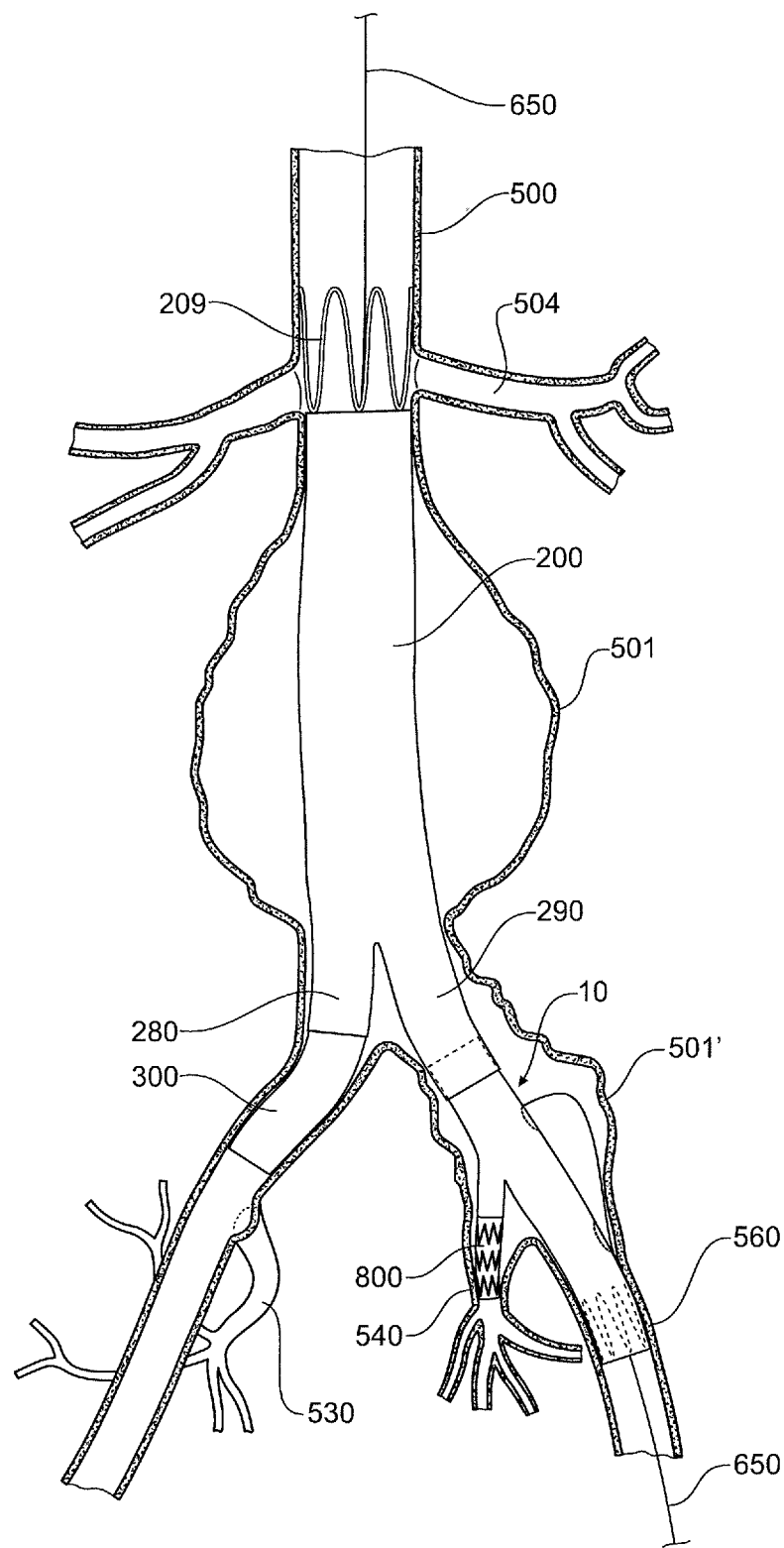

Turning now to FIGS. 6a, 6b and 6c, these figures are similar to FIGS. 5e, 5f and 5i respectively but show deployment of a stent graft 10 according to the first embodiment of the invention illustrated in FIGS. 2a to 2d being deployed.

Finally, referring to FIG. 7, this figure is similar to FIG. 5h, but shows a stent graft 10 according to a third embodiment of the invention, as illustrated in FIGS. 4a to 4c in its finally deployed state. It can be seen that in this state, the proximal sealing stent 29 has expanded to close the closable portion 49, thereby closing the entry aperture 48.

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers.

The reference to any prior art in this specification is not, and should not be taken as, an acknowledgement of any form of suggestion that such prior art forms part of the common general knowledge.

It will be appreciated by those skilled in the art that the invention is not restricted in its use to the particular application described. Neither is the present invention restricted in its preferred embodiment with regard to the particular elements and/or features described or depicted herein. It will be appreciated that the invention is not limited to the embodiment or embodiments disclosed, but is capable of numerous rearrangements, modifications and substitutions without departing from the scope of the invention as set forth and defined by the following claims.

The invention claimed is:

1. A stent graft for placement in a lumen of a patient, the stent graft comprising:
   a main tubular body of a biocompatible graft material having a main lumen, the main tubular body having a proximal end, a distal end, and a side wall between the proximal end and the distal end;
   a side arm extending from a first fenestration in the side wall of the main tubular body on one side of the main body, the side arm having a side arm lumen;

a second fenestration in the side wall of the main body positioned opposite the first fenestration, the second fenestration providing an exit aperture for a medical instrument;

a third fenestration in the side wall of the main body spaced distally from the second fenestration, the third fenestration providing an entry aperture for the medical instrument; and a cannulation pocket adjacent to and outside the lumen of the main body, the cannulation pocket enclosing the second and third fenestrations and providing an enclosed space, the cannulation pocket having a guide surface for the medical instrument;

wherein the guide surface of the pocket is configured to guide the medical instrument from the entry aperture to the exit aperture and into the main lumen of the main tubular body.

2. The stent graft of claim 1, wherein the cannulation pocket is comprised of graft material.

3. The stent graft of claim 1, wherein the guide surface is configured to facilitate guiding of the medical instrument from the main lumen of the main tubular body into the side arm lumen.

4. The stent graft of claim 1, wherein the side arm is at an acute angle to the main tubular body such that the side arm lumen extends laterally and distally from the main tubular body.

5. The stent graft of claim 4, further comprising an external self-expanding stent which extends around both the main tubular body and a portion of the side arm, the stent configured to expand such that the main lumen and the side arm lumen are each biased open allowing fluid to flow freely there-through.

6. The stent graft of claim 1, further comprising a temporary diameter reduction constraint arrangement, the arrangement comprising:
 a release wire; and
 at least one loop of thread engaged with the release wire and engaged around a distal portion of the main body to a location circumferentially spaced a selected distance away from the release wire, and drawn tight and tied to itself to reduce the distal portion of the main body.

7. The stent graft of claim 1, wherein the stent graft comprises a distal sealing portion configured to seal against a wall of a body vessel and wherein the third fenestration is disposed proximally above the sealing portion.

8. The stent graft of claim 1, wherein the medical instrument is a guidewire.

9. The stent graft of claim 1, wherein the medical instrument is a delivery device with a side arm extension graft.

10. A stent graft for placement in a lumen of a patient, the stent graft comprising:
 a main tubular body of a biocompatible graft material having a main lumen, the main tubular body having a proximal end, a distal end, and a side wall between the proximal end and the distal end;
 a side arm extending from a first fenestration in the side wall of the main tubular body on one side of the main body, the side arm having a side arm lumen;
 a second fenestration in the side wall of the main body positioned opposite the first fenestration, the second fenestration providing an exit aperture for a medical instrument;
 a cannulation pocket adjacent to and outside the lumen of the main body, the cannulation pocket providing an enclosed space extending from the distal end of the main tubular body to proximal of the second fenestration, the cannulation pocket having a distal opening adjacent to the distal end of the main tubular body providing an entry aperture for the medical instrument, and a guide surface for the medical instrument;
 wherein the guide surface of the pocket is configured to guide the medical instrument from the entry aperture to the exit aperture and into the main lumen of the main tubular body.

11. The stent graft of claim 10, further comprising a self-expanding stent disposed about the distal end of the main tubular body.

12. The stent graft of claim 11, wherein the self-expanding stent is configured to close the distal opening of the cannulation pocket upon expansion of the self-expanding stent.

13. The stent graft of claim 10, wherein the cannulation pocket is comprised of graft material.

14. The stent graft of claim 10, wherein the guide surface is configured to facilitate guiding of the medical instrument from the main lumen of the main tubular body into the side arm lumen.

15. The stent graft of claim 10, wherein the side arm is at an acute angle to the main tubular body such that the side arm lumen extends laterally and distally from the main tubular body.

16. The stent graft of claim 15, further comprising an external self-expanding stent which extends around both the main tubular body and a portion of the side arm, the stent configured to expand such that the main lumen and the side arm lumen are each biased open allowing fluid to flow freely there-through.

17. The stent graft of claim 10, further comprising a temporary diameter reduction constraint arrangement, the arrangement comprising:
 a release wire; and
 at least one loop of thread engaged with the release wire and engaged around a distal portion of the main body to a location circumferentially spaced a selected distance away from the release wire, and drawn tight and tied to itself to reduce the distal portion of the main body.

18. The stent graft of claim 10, wherein the medical instrument is a guidewire.

19. The stent graft of claim 1, wherein the medical instrument is a delivery device with a side arm extension graft.

20. A stent graft assembly for placement in a lumen of a patient, the stent graft assembly comprising a stent graft and a pre-loaded medical instrument, the stent graft comprising:
 a main tubular body of a biocompatible graft material having a main lumen, a proximal end, a distal end, a side wall of graft material between the proximal end and the distal end, a side arm extending from the side wall on one side of the main tubular body, and a fenestration in the side wall substantially opposite the side arm providing,
 a cannulation pocket attached to and adjacent the side wall of the main tubular body, the cannulation pocket providing an enclosed space enclosing a portion of the side wall and the fenestration, the cannulation pocket having a guide surface configured to guide a medical instrument from an entry aperture disposed distally of the fenestration into the enclosed space of the cannulation pocket to the fenestration and into the main lumen main tubular body;
 wherein the pre-loaded guidewire is loaded on a delivery device with the stent graft and, in the pre-loaded state, extends through the entry aperture, into the enclosed space of the cannulation pocket, substantially along the guide surface, through the fenestration, into the lumen of the main body, and into the side arm lumen.

* * * * *